(12) United States Patent
Newton et al.

(10) Patent No.: US 6,491,625 B1
(45) Date of Patent: Dec. 10, 2002

(54) ENDOSCOPY TESTING APPARATUS AND METHOD

(75) Inventors: William Charles Brian Newton, Greensboro, NC (US); Bradly Lawrence Jensen, Greensboro, NC (US)

(73) Assignee: The Scope Exchange, Inc., Kernersville, NC (US)

( * ) Notice: Subject to any disclaimer, the term of this patent is extended or adjusted under 35 U.S.C. 154(b) by 0 days.

(21) Appl. No.: 09/535,248

(22) Filed: Mar. 27, 2000

(51) Int. Cl.[7] .................................. A61B 1/04
(52) U.S. Cl. ................. 600/133; 73/45.5; 73/865.9; 128/898
(58) Field of Search ................. 600/132, 133, 600/101; 73/865.9, 45.5, 40; 128/898

(56) References Cited

U.S. PATENT DOCUMENTS

| | | | |
|---|---|---|---|
| 4,216,767 A | 8/1980 | Aoshiro ..................... | 128/6 |
| 4,240,411 A | 12/1980 | Hosono ..................... | 128/4 |
| 4,241,729 A | 12/1980 | Aoshiro ..................... | 128/4 |
| 4,404,963 A | 9/1983 | Kohri ....................... | 128/4 |
| 4,545,369 A | 10/1985 | Sato ......................... | 128/4 |
| 4,574,783 A | 3/1986 | Kazuhiro et al. ........... | 128/4 |
| 4,742,818 A | 5/1988 | Hughes et al. ............. | 128/6 |
| 4,858,001 A | 8/1989 | Milbank et al. ............ | 358/98 |
| 4,874,364 A | 10/1989 | Morris et al. .............. | 604/35 |
| 4,878,484 A | 11/1989 | Miyagi ...................... | 128/4 |
| 5,447,148 A | 9/1995 | Oneda et al. .............. | 600/131 |
| 5,807,238 A | 9/1998 | Feldman et al. ........... | 600/133 |
| 5,868,667 A | 2/1999 | Lin et al. .................. | 600/133 |

OTHER PUBLICATIONS

Evis Gastrointestinal Videoscope/Colonovideoscope/ Sigmoidovideoscope Instructions Manual, Olympus Corporation, believed to be prior art.
Evis Colonovideoscope Instructions Manual, Olympus Corporation, believed to be prior art.

*Primary Examiner*—John P. Leubecker
*Assistant Examiner*—Jocelyn Ram
(74) *Attorney, Agent, or Firm*—Womble Carlyle Sandridge & Rice, PLLC

(57) ABSTRACT

The present invention is a cap tester for a water resistant cap for medical video equipment that comprises a neck capable of insertion within the cap. The neck has an air duct extending therethrough. Preferably, the neck further comprises at least one projection extending outwardly from the neck. The projection mates with interior grooves of the cap to releasably connect the cap tester to the cap. A collar extends outwardly beyond the neck to provide a cover to the neck upon insertion into the cap. A conduit extends above the collar and substantially aligns with the duct within the neck that may be connected to a positive air supply. Thus, upon placing a cap tester within the cap, the method of the present invention comprises pressurizing the cap and cap tester, submersing the cap and cap tester in liquid and observing the immersed cap and cap tester for air bubbles thereby indicating a leak in either the cap frame or any seal located therein.

30 Claims, 3 Drawing Sheets

ENDOSCOPY TESTING APPARATUS AND METHOD

FIELD OF THE INVENTION

The invention relates generally to the field of endoscopes and more specifically to an apparatus and method for testing the water resistant caps used in the reprocessing of endoscopes and other medical video equipment that require such water resistant caps.

BACKGROUND OF THE INVENTION

Video cameras and endoscopes are used in a variety of surgical procedures. An endoscope provides the operator with internal electro-visual inspection of a particular area of interest within a patient. Endoscopes are generally equipped with accessories that allow the operator to collect biopsy or tissue samples or repair damage through electrosurgery.

One common configuration of an endoscope includes a connector component and a control component. The control component generally includes the various operator controls for the instrument, for example, controls for the light and video components as well as the biopsy forceps. The connector component includes connections for inter alia the light source, the air and water inlets, the suction source, as well as the electrical connections for the videoscope cable. Although the particular endoscope described above is used as an example, the present invention relates to any applicable surgical video device.

Cleaning, disinfecting, and sterilization (hereinafter collectively referred to as "reprocessing") of endoscopes allows for repeated uses. The electrical connector for the video cable is not waterproof and must be covered with a water-resistant cap before washing or immersion of the endoscope. Otherwise the endoscope will be damaged requiring costly repair or replacement. The water resistant cap is attached to the electrical connector on the endoscope to protect the connector from water penetration during reprocessing. The water resistant cap resists fluid from entering the endoscope (or other applicable medical instrument) or contacting the electrical connections thereof during reprocessing.

Prior to reprocessing, endoscopes are leak tested to detect leaks before any fluid invasion occurs, thereby reducing repair costs. For leakage testing, the water resistant cap is configured for connection to a leakage tester. As a non-limiting example, the cap may be configured with a venting connector. The leakage tester supplies pressurized air to the endoscope via the water resistant cap. Thus, the endoscope (with the water resistant cap correctly attached) is submerged in water with a positive air pressure applied. The endoscope is flagged as defective if air bubbles emanate from the endoscope. Unfortunately, however, this test does not account for each component of the endoscope. Notably, the foregoing test does not test for leaks in the water resistant cap, itself A defective water resistant cap can cause great damage to an otherwise acceptable endoscope as a result of the reprocessing process. This damage results from leakage from the defective cap into the electrical and video connectors.

The above-described test provides positive air pressure. Thus, the configuration of the connection between the leakage tester and the water resistant cap requires a sealed environment. Any seals within the cap that are not waterproof are not detectable. For example, the water resistant cap may have an inner O-ring seal that is not affected by the above-described leakage test.

Currently, the water resistant cap is inspected through visual inspection only. The inside of the cap is checked for dryness and an inspector inspects the seal inside the cap for visible scratches, flaws or debris. There is a need, therefore, for an effective apparatus and method for testing the water resistant cap of an endoscope apparatus, including both the frame of the cap as well as the interior seals. As discussed above, the ability to detect leaks will prevent costly damage to the electrical connections of the endoscopy equipment.

SUMMARY OF THE INVENTION

The present invention is a cap tester for a water resistant cap that addresses the aforementioned deficiencies in current testing procedures.

The present invention is a cap tester for a water resistant cap for medical video equipment that comprises a neck capable of insertion within the cap. The neck has an air duct extending therethrough. Preferably, the neck further comprises at least one projection extending outwardly from the neck. The projection mates with interior grooves of the cap to releasably connect the cap tester to the cap. A collar extends outwardly beyond the neck to provide a cover to the neck upon insertion into the cap. A conduit extends above the collar and substantially aligns with the duct within the neck that may be connected to a positive air supply. Thus, upon placing a cap tester within the cap, the method of the present invention comprises pressurizing the cap and cap tester, submersing the cap and cap tester in liquid and observing the immersed cap and cap tester for air bubbles thereby indicating a leak in either the cap frame or any seal located therein.

The present invention also comprises a method for testing a cap comprising placing a cap tester within the cap, pressurizing the cap and cap tester, submersing the cap and cap tester in liquid and observing the immersed cap and cap tester for air bubbles thereby indicating a leak.

A further embodiment of the present invention comprises a cap tester for a water resistant cap, the cap having a cavity for medical video equipment. The cap tester comprises a housing, a first aperture and a second aperture in the housing, such that the housing sealably connects to the water resistant cap. The first and second apertures are fluidly connected to allow for the application of a positive pressure through the first and second apertures. Further, the second aperture is open to the cap to form a positive pressure within the cavity of the cap for leak detection purposes.

These and other aspects of the present invention as disclosed herein will become apparent to those skilled in the art after a reading of the following description of the preferred embodiments when considered with the drawings. The drawings are for the purpose of describing a preferred embodiment of the invention and are not intended to limit the present invention.

DETAILED DESCRIPTION OF THE PREFERRED EMBODIMENT

Figure 1:
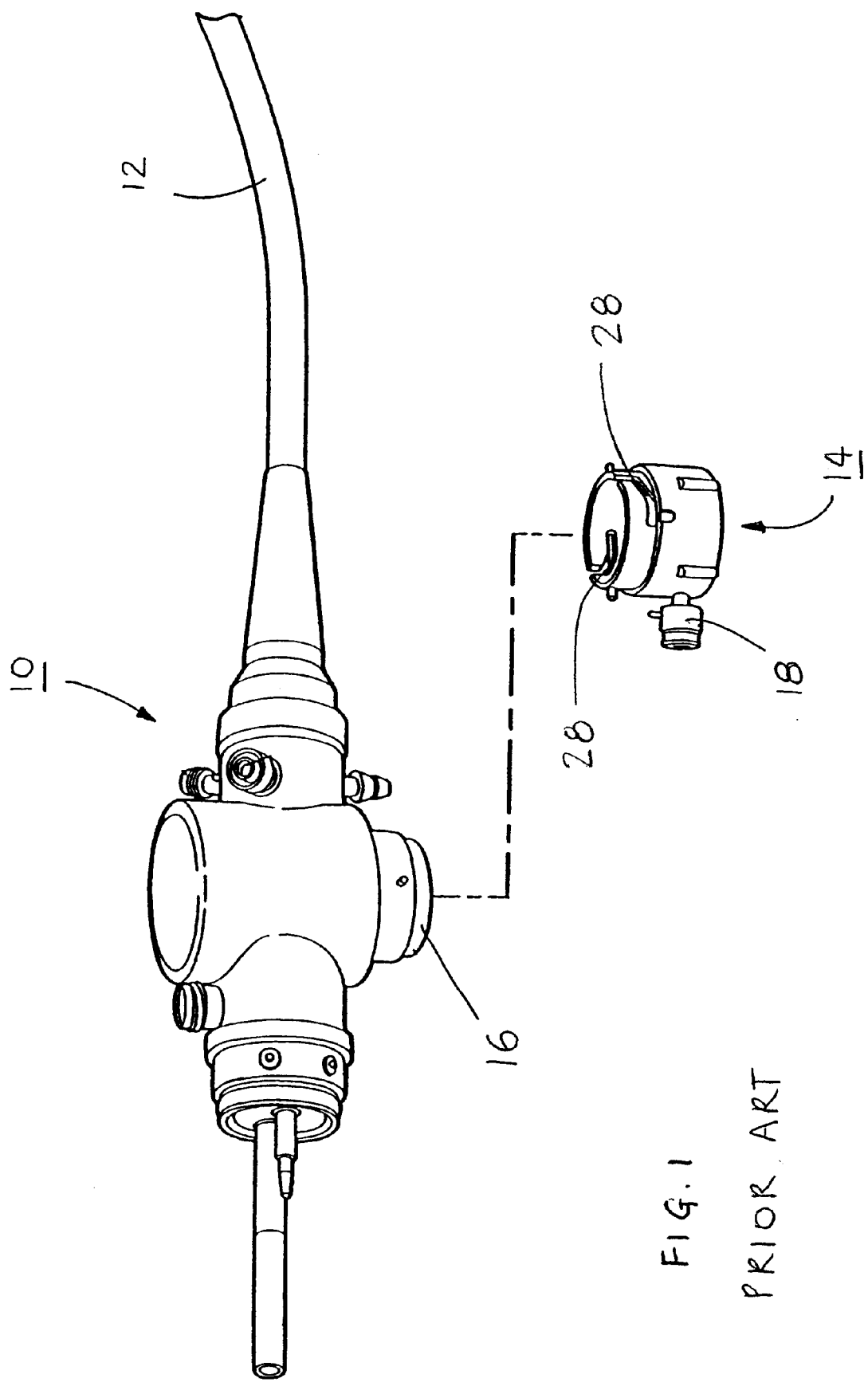
FIG. 1 is an exploded view of a connector section of an endoscopy apparatus.

The present invention relates generally to endoscopes and other medical video equipment that use caps. FIG. 1 illustrates a connector section 10 of a common endoscope, such as an Olympus CF Type 1T100L/I Evis Colonovideoscope, sold by Olympus Corporation, Lake Success, N.Y. The connector component 10 connects to the control component via the universal cord 12. As described above, a cap 14 is placed upon the electrical connector 16 prior to reprocessing. Although we illustrate this invention with an Olympus cap as an example, this invention should not be limited to Olympus caps, i.e. caps manufactured by other vendors such as Pentax and Fujinon may be tested with the present invention.

The electrical connector 16 is not waterproof and must be covered with the cap 14 prior to reprocessing. The cap 14 may include a venting connector 18 that accepts the leakage connector (not shown) to detect any water leak in the endoscope before any fluid invasion occurs. As referenced above, the cap 14 may be configured differently from the Olympus model and the scope of the present invention includes use of the present invention with any cap configuration. For example, the cap may have an inner O-ring seal and not be configured with a venting connector.

The leakage connector supplies pressurized air through the cap 14 and the instrument is immersed in liquid and observed for air bubbles. Thus, the leakage connector covers the venting connector 18 during leak-testing procedures to insure the flow of pressurized air.

Figure 2:
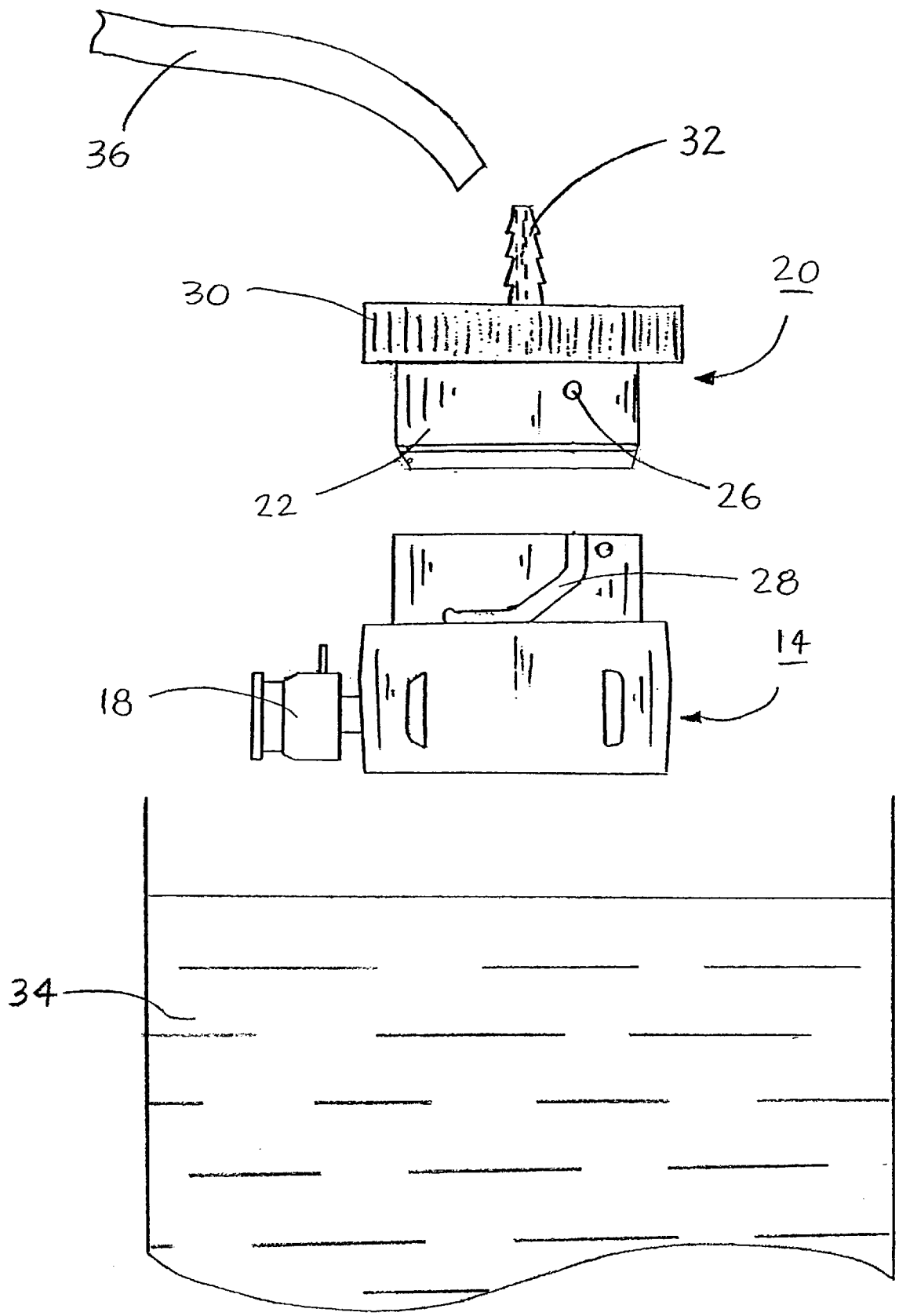
FIG. 2 is an exploded view of an embodiment of the present invention illustrated as used in conjunction with the cap.
Figure 3:
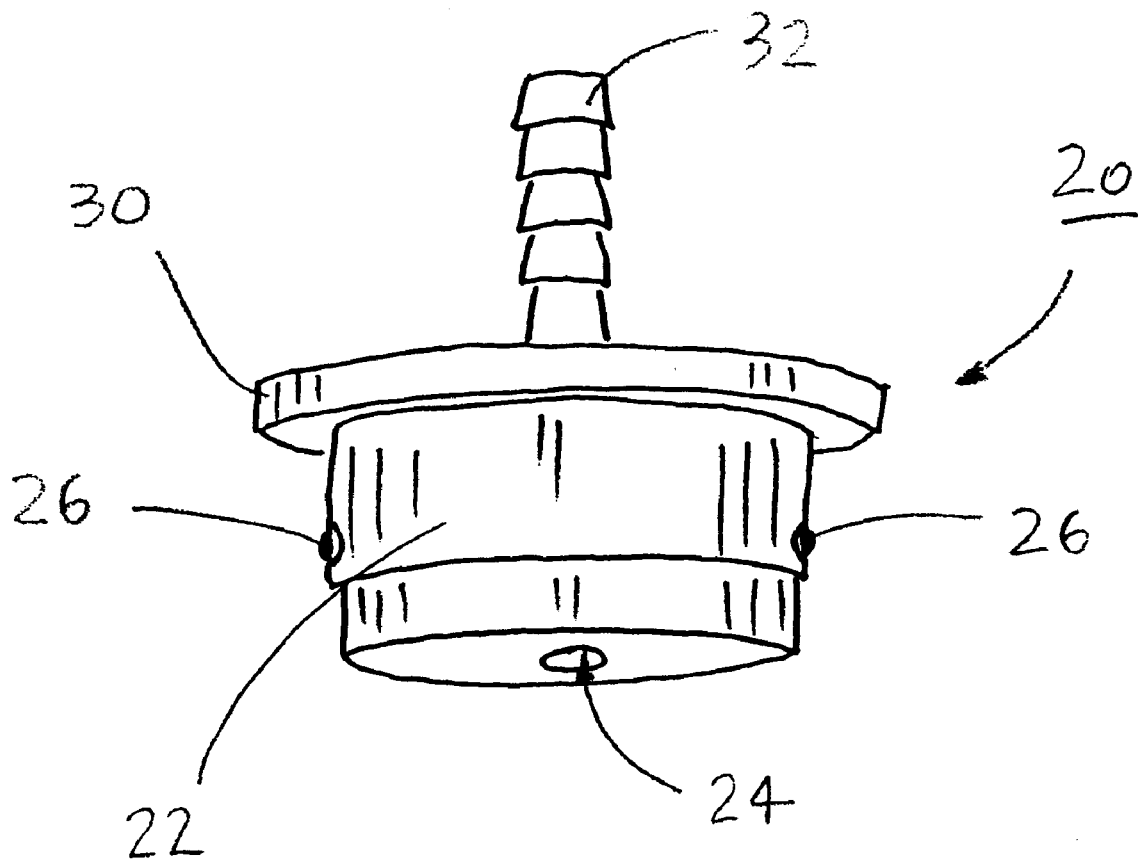
FIG. 3 is a perspective view of an embodiment of the present invention.

The present invention comprises a cap tester 20 for the cap 14. The cap tester comprises a neck 22 capable of insertion within a cap. As illustrated in the Figures, caps generally are cylindrical, therefore, preferably the cap tester is also substantially cylindrical. Also, preferably, the neck extends downwardly inwardly as illustrated in FIGS. 2 and 3, to provide ease of insertion into the cap 14. The inward configuration may be through a constant inward slope or through consecutive inward steps. The cap tester 20, however, may be any appropriate shape to conform to the interior of the cap 14 such as to create a sealed environment between the cap tester 20 and the cap 14. Similarly, although any appropriate material may be used, preferably the cap tester 14 is formed of stainless steel. Such material assists in avoiding problems associated with the cap tester itself having a frame or seal leak to complicate the test procedure.

The neck 22 houses a duct 24. The dimension of the duct must allow sufficient air to flow through the cap tester 20 into the cap 14. The preferred air pressure is approximately 180–200 mm Hg or 3.5 to 4.25 psi. The preferred dimensions of the duct 24 are about 0.80 to 0.125 inner diameter by 0.180 to 0.25 outer diameter and about 0.375 to 0.5 inches in length. The dimensions of neck 22 vary depending upon the cap to be tested. Such dimensions are readily determinable through correlation with the cap to be tested.

The cap tester 20 should be releasably sealable within the cap 14. Any suitable mating method can be employed depending upon the configuration of the cap 14. A preferred configuration of the neck 22 has at least one projection 26 for releasable engagement with at least one of the interior grooves 28 of the cap 14. The preferred configuration imitates the electrical connector 16 sealing interface. The neck can also have two projections on diametrically opposing sides, as illustrated in FIG. 3. The projections 26 mate with interior grooves 28 of the cap 14 to releasably connect the cap tester 20 to the cap 14. The interface between the cap and cap tester should be a substantially tight seal as not to create leakage of air upon forced pressure through duct 24. Preferably, however, no additional sealing structure, such as an o-ring seal, is required due to the possibility of the seal developing cracks or other deformities and creating leaks, themselves. Preferably, the cap tester 20 is machined to the specifications of the cap to be tested. Although a preferred configuration is described, other configurations that create a sealed engagement between the neck 22 and the cap 14 are within the scope of this invention.

A collar 30 extends outwardly beyond the neck 22 to provide a cover to the neck 22 upon insertion into the cap 14.

The collar 30 provides a cover to maintain an air-tight environment upon insertion of the neck 22 into the cap 14. Further, the collar 30 acts as a stop for insertion of the neck 22 within the cap 14.

Lastly, the cap tester has an air conduit 32. The preferred conduit 32 is illustrated in FIG. 2 and extends above the collar 30 and substantially aligns with the duct 24 that extends through the neck 22. Preferably, the conduit 32 is barbed to ensure engagement of the conduit 32 with an air supply hose 36 that is connected to any appropriate air supply, such as a hand held or electrical pump as are known in the art.

In use for testing a cap 14, a tester should first visually inspect the cap tester 20 and cap 14 for visible deformities. Then, the cap tester 20 is placed within the cap 14 and releasably locked within the cap 14 by engagement of the projection(s) 26 with the interior grooves 28. Thereafter, the air supply is connected to the conduit 32 via the air supply hose 36. The cap 14 and cap tester 20 are pressurized and submersed in liquid 34. The preferred air pressure as stated earlier is approximately 180–200 mm Hg or 3.5 to 4.25 psi, but any appropriate positive air pressure may be used.

The tester observes the immersed and pressurized cap 14 and cap tester 20 as they are sealed together for air bubbles, thereby indicating a leak in either the frame or the seals of the cap 14. Preferably the tester conducts the test for approximately 2 to 5 minutes and looks for a steady stream of bubbles. If bubbles are visible, then the cap 14 is not water-resistant and must be repaired or replaced.

Although specific embodiments of the present invention have been illustrated and described in detail, it is to be expressly understood that the invention is not limited thereto. The above detailed description of the embodiment is provided for example only and should not be construed as constituting any limitation of the invention. Modifications will be obvious to those skilled in the art, and all modifications that do not depart from the spirit of the invention are intended to be included within the scope of the appended claims.

What is claimed is:

1. A cap tester for a water resistant cap for medical video equipment, the cap tester comprising:
   a neck configured to releasably engage an interior portion of the water resistant cap;
   a duct extending through the neck; and
   an air conduit that substantially aligns with the duct of the neck;
   wherein when the neck is inserted in the water resistant cap and then immersed in liquid, air supplied through the conduit flows through the duct into the cap to detect defects in the water resistance of the water resistant cap.

2. The cap tester of claim 1 wherein the water resistant cap includes at least one interior groove, the cap tester further comprising:
   at least one projection extending outwardly from the neck, wherein the at least one projection mates with the at least one interior groove of the cap to releasably connect the cap tester with the cap.

3. The cap tester of claim 2 wherein two projections extend outwardly from the neck and are located on opposite sides of the neck.

4. The cap tester of claim 1 further comprising:
   a collar that extends upwardly above the neck and extends outwardly beyond the neck to provide a cover to the neck upon insertion into the cap.

5. The cap tester of claim 4 wherein as the neck extends downwardly from the collar, it also extends inwardly.

6. The cap tester of claim 1 wherein the cap and cap tester are substantially cylindrical.

7. The cap tester of claim 1 wherein the conduit is barbed.

8. The cap tester of claim 1 wherein the cap tester is formed of stainless steel.

9. A method for testing a cap comprising:

placing a cap tester within the cap;

pressurizing the cap and cap tester;

submersing the cap and cap tester in liquid;

observing the immersed cap and cap tester for air bubbles thereby indicating a leak.

10. The method of claim 9 further comprising:

releasably locking the cap tester within the cap.

11. The method of claim 9 wherein the pressure is about 180 to 220 mm Hg.

12. The method of claim 9 wherein the pressure is about 3.5 to 4.25 psi.

13. The method of claim 9 wherein the method further comprises visually inspecting the cap and cap tester for visible deformities.

14. A cap tester for a water resistant cap of video medical equipment, the cap tester comprising:

means for connecting the cap tester to an inner portion of the water resistant cap; and air supply means for supplying air through the cap tester, wherein air is capable of flowing through the cap tester into the water resistant cap such that upon immersion in liquid defects in the water resistance of the water resistant cap are detectable.

15. The cap tester of claim 14 further comprising:

releasable locking means to releasably lock the cap and cap tester together.

16. The cap tester of claim 14 further comprising:

sealing means to ensure a sealed relationship between the cap and cap tester.

17. A method for reprocessing medical video equipment having a electric connector comprising:

performing an immersion leak test on a water resistant cap;

attaching the water resistant cap to the electrical connector; and performing an immersion leak test on the medical video equipment.

18. The method of claim 17 further comprising:

visually inspecting the water resistant cap.

19. The method of claim 17 further comprising:

drying the water resistant cap sufficiently before attaching the cap to the electrical connector.

20. A cap tester for a water resistant cap having a cavity for medical video equipment, the cap tester comprising:

a housing;

a first aperture in the housing;

a second aperture in the housing;

wherein the housing sealably connects to an inner portion of the water resistant cap, and the first and second aperture are fluidly connected to allow for the application of a positive pressure to be supplied through the first aperture and second aperture, and the second aperture is open to the water resistant cap to form a positive pressure within the cavity of the water resistant cap for leak detection purposes.

21. The cap tester of claim 20 wherein the first aperture further comprises a tube that extends beyond the housing to allow for connection with a positive air pressure source.

22. The cap tester of claim 21 wherein the tube of the first aperture has a length of approximately 0.375 to 0.50 inches and has an inner diameter of 0.80 to 0.125 inches and an outer diameter of 0.180 to 0.25 inches.

23. The cap tester of claim 20 wherein the housing further comprises at least one projection that releasably mates with at least one interior groove within the cavity to form a locking connection.

24. The cap tester of claim 20 wherein at least a portion of the housing has a shape that corresponds to the cavity of the water resistant cap.

25. The cap tester of claim 20 wherein the positive air pressure applied is approximately 3.5 to 4.25 psi.

26. The cap tester of claim 20 wherein the positive air pressure applied is approximately 180–200 mm Hg.

27. The cap tester of claim 20 wherein the medical video equipment is an endoscope.

28. A cap tester for a water resistant cap for medical video equipment, the cap tester comprising:

a neck configured to rotatably engage an interior portion of the water resistant cap;

a duct extending through the neck; and an air conduit that substantially aligns with the duct of the neck; wherein when the neck is inserted in the water resistant cap and then immersed in liquid, air supplied through the conduit flows through the duct into the cap to detect defects in the water resistance of the water resistant cap.

29. A cap tester for a water resistant cap having a cavity for medical video equipment, the cap tester comprising:

a stainless steel housing;

a first aperture in the housing;

a second aperture in the housing; wherein the housing sealably connects to an inner portion of the water resistant cap, and the first and second aperture are fluidly connected to allow for the application of a positive pressure to be supplied through the first aperture and second aperture, and the second aperture is open to the water resistant cap to form a positive pressure within the cavity of the water resistant cap for leak detection purposes.

30. A cap tester for a water resistant cap having a cavity for medical video equipment, the cap tester comprising:

a housing configured to replicate at least a portion of an electrical connector of an endoscope;

a first aperture in the housing;

a second aperture in the housing; wherein the housing sealably connects to an inner portion of the water resistant cap, and the first and second aperture are fluidly connected to allow for the application of a positive pressure to be supplied through the first aperture and second aperture, and the second aperture is open to the water resistant cap to form a positive pressure within the cavity of the water resistant cap for leak detection purposes.

* * * * *